(12) United States Patent
Axel et al.

(10) Patent No.: US 10,545,208 B2
(45) Date of Patent: Jan. 28, 2020

(54) SYSTEM, METHOD AND COMPUTER-ACCESSIBLE MEDIUM FOR RAPID REAL-TIME CARDIAC MAGNETIC RESONANCE IMAGING UTILIZING SYNCHRONIZED CARDIO-RESPIRATORY SPARSITY

(71) Applicant: New York University, New York, NY (US)

(72) Inventors: Leon Axel, New York, NY (US); Li Feng, New York, NY (US); Ricardo Otazo, New York, NY (US); Daniel Sodickson, Larchmont, NY (US)

(73) Assignee: New York University, New York, NY (US)

( * ) Notice: Subject to any disclaimer, the term of this patent is extended or adjusted under 35 U.S.C. 154(b) by 1238 days.

(21) Appl. No.: 14/697,099

(22) Filed: Apr. 27, 2015

(65) Prior Publication Data

US 2015/0309135 A1 Oct. 29, 2015

Related U.S. Application Data

(60) Provisional application No. 61/984,364, filed on Apr. 25, 2014.

(51) Int. Cl.
*G01R 33/48* (2006.01)
*G01R 33/565* (2006.01)
(Continued)

(52) U.S. Cl.
CPC ........ *G01R 33/4824* (2013.01); *A61B 5/0044* (2013.01); *A61B 5/055* (2013.01);
(Continued)

(58) Field of Classification Search
CPC .......... G01R 33/4824; G01R 33/56509; G01R 33/5673; G01R 33/56325; A61B 5/0044; A61B 5/055; A61B 5/7289
See application file for complete search history.

(56) References Cited

U.S. PATENT DOCUMENTS

| 8,675,942 B2 * | 3/2014 | Chang ................ G01R 33/4824 382/131 |
| 9,113,810 B2 * | 8/2015 | Edelman ................ A61B 5/055 |
| 2017/0307714 A1 * | 10/2017 | Okell ............... G01R 33/56366 |

OTHER PUBLICATIONS

Carr, James C. et al., "Cine MR Angiography of the Heart with Segmented True Fast Imaging with Steady-State Precession," Radiology, vol. 219, pp. 828-834, 2001.
(Continued)

*Primary Examiner* — Dixomara Vargas
(74) *Attorney, Agent, or Firm* — Hunton Andrews Kurth LLP

(57) ABSTRACT

An exemplary system, method and computer-accessible medium can be provided for generating an image(s) of a tissue(s) that can include, for example, receiving magnetic resonance imaging information regarding the tissue(s) based on a golden-angle radial sampling procedure, sorting and synchronizing the MRI information into at least two dimensions, and generating the image(s) of the tissue(s) based on the sorted and synchronized information. The tissue(s) include cardiac tissue and respiratory-affected tissue. The MRI information can include a motion of the cardiac tissue and a motion of the respiratory tissue.

23 Claims, 8 Drawing Sheets

(51) Int. Cl.
    G01R 33/567    (2006.01)
    A61B 5/00      (2006.01)
    A61B 5/055     (2006.01)
    G01R 33/563    (2006.01)

(52) U.S. Cl.
    CPC ........ *A61B 5/7289* (2013.01); *G01R 33/5673* (2013.01); *G01R 33/56325* (2013.01); *G01R 33/56509* (2013.01); *A61B 5/7207* (2013.01)

(56) References Cited

OTHER PUBLICATIONS

Hansen, Michael S. et al., "Retroscpective Reconstruction of High Temporal Resolution Cine Images from Real Time MRI Using Iterative Motion Correction," Magnetic Resonance in Medicine, vol. 68, pp. 741-750, 2012.

Usman, Muhammad et al., "Motion Corrected Compressed Sensing for Free-Breathing Dynamic Cardiac MRI," Magnetic Resonance in Medicine, vol. 70, pp. 504-516, 2013.

Koeppe, Sabrina et al., "MR-Based Analysis of Regional Cardiac Function in Relation to Cellular Integrity in Fabry Disease," International Journal of Cardiology, vol. 160, pp. 53-58, 2012.

Feng, Li et al., "Highly Accelerated Real-Time Cardiac Cine MRI Using k-t Sparse-Sense," Magnetic Resonance in Medicine, vol. 70, pp. 64-74, 2013.

Otazo, Ricardo et al., "Combination of Compressed Sensing and Parallel Imaging of Highly Accelerated First-Pass Cardiac Perfusion MRI," Magnetic Resonance in Medicine, vol. 64, pp. 767-775, 2010.

Liu, Jing et al., "Respiratory and Cardiac Self-Gated Free-Breathing Cardiac CINE Imaging with Multiecho 3D Hybrid Radial SSFP Acquisition," Magnetic Resonance in Medicine, vol. 63, pp. Dec. 30, 1237, 2010.

Fessler, Jeffrey A. et al., "Nonuniform Fast Fourier Transforms Using Min-Max Interpolation," IEEE T-SP, vol. 51, No. 2, pp. 560-574, Feb. 2003.

Feng, Li et al., "High Spatial and Temporal Resolution 2D Real Time and 3D Whole-Heart Cardiac Cine MRI Using Compressed Sensing and Parallel Imaging with Golden Angle Radial Trajectory," Proc. Intl. Soc. Mag. Reson. Med. vol. 20, p. 225, 2012.

Feng, Li et al., "Compressed Sensing Reconstruction with an Additional Respiratory-Phase Dimension for Free Breathing Imaging," Proc. Intl. Soc. Mag. Reson. Med., vol. 21, p. 606, 2013.

Feng, Li et al., "Evalutaing both "Normal" and Ectopic Cardiac Cycles in Patients with Arrhythmias Using Free-Breathing Compressed Sensing MRI with Physiological Motion Snychronization," Proc. Intl. Soc. Mag. Reson. Med., vol. 22, 2014.

Beer, Meinrad et al., "Free Breathing Cardiac Real-Time Cine MR Without ECG Triggering," Int. Journal of Cardiol. pp. 380-382, 2010.

Feng, Li et al., "Golden-Angle Radial Sparse Parallel MRI: Combination of Compressed Sensing, Parallel Imaging, and Golden-Angle Radial Sampling for Fast and Flexible Dynamic Volumetric MRI," Magnetic Resonance in Medicine, vol. 72, pp. 707-717, 2014.

* cited by examiner

SYSTEM, METHOD AND COMPUTER-ACCESSIBLE MEDIUM FOR RAPID REAL-TIME CARDIAC MAGNETIC RESONANCE IMAGING UTILIZING SYNCHRONIZED CARDIO-RESPIRATORY SPARSITY

CROSS-REFERENCE TO RELATED APPLICATION(S)

This application relates to and claims priority from U.S. Patent Application No. 61/984,364, filed on Apr. 25, 2014, the entire disclosure of which is incorporated herein by reference.

FIELD OF THE DISCLOSURE

The present disclosure relates generally to magnetic resonance imaging ("MRI"), and more specifically, to exemplary embodiments of an exemplary system, method and computer-accessible medium for rapid real-time cardiac MRI utilizing synchronized cardio-respiratory sparsity.

BACKGROUND INFORMATION

Breath-hold balanced-Steady-State Free Precession (b-"SSFP") cine imaging can be considered the gold standard for evaluating myocardial function in MRI. (See, e.g., Reference 1). However, the performance of breath-hold cine MRI can be degraded in patients with impaired breath-hold capability, due to failure to synchronize cardiac cycles at different respiratory states. In order to minimize the influence from respiration, a deformable registration framework has been incorporated into reconstruction for respiratory motion correction (see, e.g., References 2 and 3); however it ran the risk of introducing spatial blurring due to interpolation errors. Real-time cine MRI procedure is an alternative which can facilitate free-breathing imaging at the expense of lower spatial resolution (see, e.g., Reference 4). Compressed sensing techniques exploiting temporal sparsity have enabled higher spatiotemporal resolutions for real-time cine MRI. (See, e.g., Reference 5). However, the superposition of respiratory and cardiac motion limits temporal sparsity.

Evaluation of myocardial function with MRI can be challenging in patients with arrhythmias, such as premature ventricular contractions ("PVCs") or atrial fibrillation, due to the difficulty of synchronizing disparate cardiac cycles. In order to achieve adequate image quality in these patients, the electrocardiogram ("ECG") signal can usually be monitored such that the "ectopic" cardiac cycles can be discarded before image synchronization and reconstruction. However, those discarded "ectopic" cardiac cycles could potentially provide clinically useful information for specific cardiac diseases. For example, it is known that the premature ventricular contractions in PVC patients have a different pattern than the normal ventricular contractions. Therefore it can be clinically useful if both "normal" and "ectopic" cardiac cycles can be reconstructed for clinical use. The application of compressed sensing to real-time cine imaging can be a promising tool to enable free-breathing real-time cine imaging with adequate spatiotemporal resolution on patients with impaired breath-hold capabilities or arrhythmias. (See, e.g., References 10 and 11). However, conventional temporal compressed sensing does not account for respiratory motion or arrhythmias, and thus only moderate performance can be achieved in these cases.

Thus, it may be beneficial to provide an exemplary system, method and computer-accessible medium for rapid real-time cardiac MRI that can address and/or overcome at least some of the deficiencies described herein above.

SUMMARY OF EXEMPLARY EMBODIMENTS

An exemplary system, method and computer-accessible medium can be provided for generating an image(s) of a tissue(s) that can include, for example, receiving magnetic resonance imaging information regarding the tissue(s) can based on a golden-angle radial sampling procedure, sorting and synchronizing the MRI information into at least two dimensions, which can be motion-related dimensions, and generating the image(s) of the tissue(s) based on the sorted and synchronized information. The tissue(s) can include cardiac tissue and respiratory tissues (e.g., respiratory-affected tissue). The MRI information can include both motion of the cardiac tissue and motion of the respiratory tissue.

In some exemplary embodiments of the present disclosure, the dimensions can be two separated dimensions. The image(s) can be generated based on a compressed sensing procedure, which can be a joint multi-coil compressed sensing procedure. The compressed sensing procedure can optionally be performed on both of the dimensions, on one of the dimensions or on a higher number of the dimensions. The tissue(s) can include cardiac tissue and respiratory tissue, or other tissue affected by cardiac or respiratory motion, and the sparsity constraints for the cardiac tissue can be different than the sparsity constraints for the respiratory tissue. The dimensions can include two motion related dimensions.

In certain exemplary embodiments of the present disclosure, the sorting procedure can include sorting based on a length of a cardiac cycle(s) of a patient to whom the tissue(s) belongs. The sorting procedure can also include sorting based on a respiratory dimension of the patient. The respiratory dimension can be from an expiration to an inspiration of the patient. The golden-angle radial sampling procedure can be a golden-angle radial k-space sampling procedure. A residual streaking artifact(s) can be removed from the image(s), which can be performed using (i) a 5th order temporal filter or (ii) a 5th order median filter.

A further exemplary embodiment of the present disclosure can include an exemplary system, method and computer-accessible medium for generating an image(s) of a tissue(s), which can include, for example, receiving imaging information regarding the tissue(s) based on a radial sampling procedure, sorting and synchronizing the imaging information into at least two dimensions, and generating the image(s) of the tissue(s) based on the sorted and synchronized information. The imaging information can include (i) magnetic resonance imaging information, (ii) positron emission tomography information, (iii) computed tomography information or (iv) single-photon emission computed tomography information. The radial sampling procedure can include a golden-angle radial sampling procedure.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figures 1A, 1B, 1C:
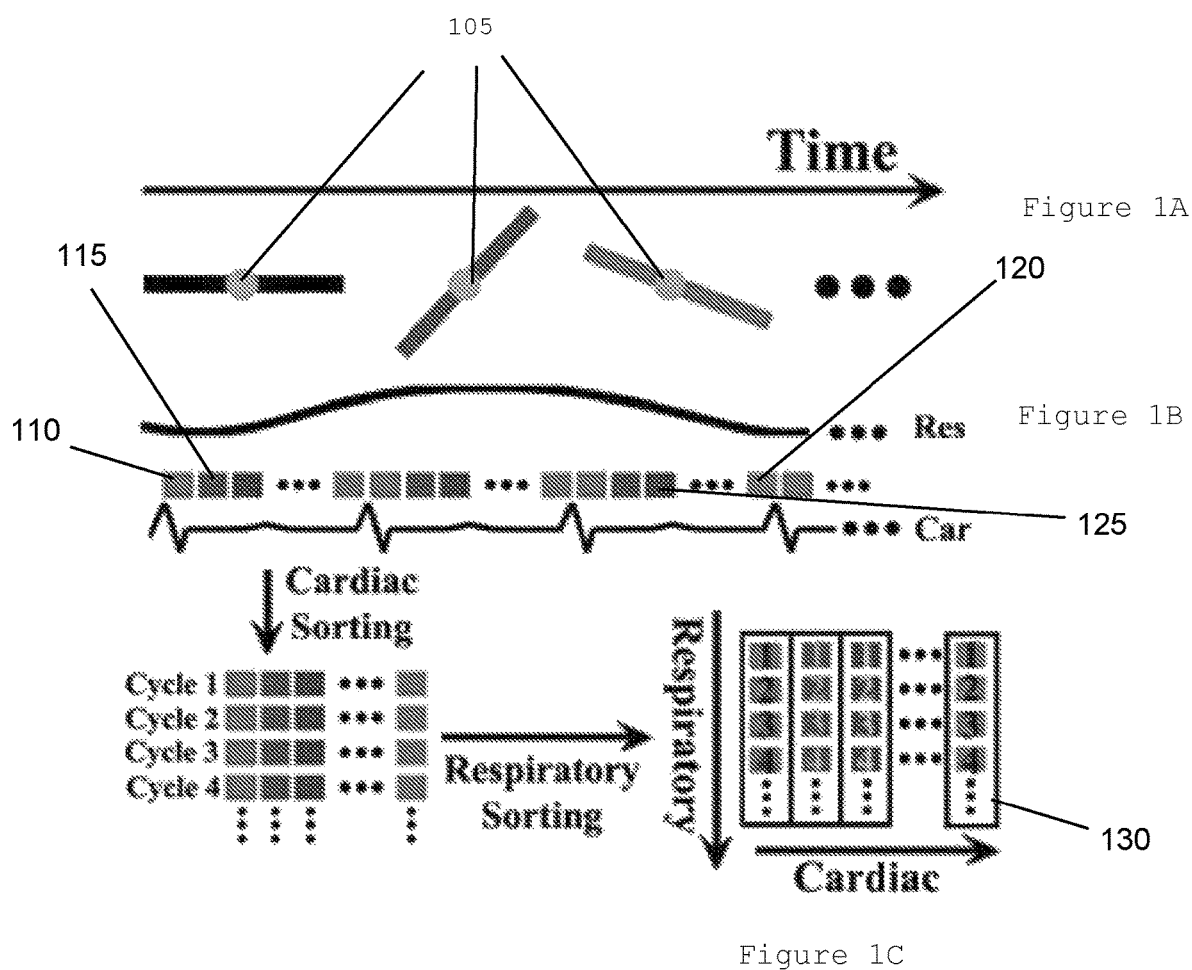
FIG. 1A is an exemplary diagram illustrating continuous data acquisition according to an exemplary embodiment of the present disclosure.
FIG. 1B is an exemplary diagram illustrating cardiac and respiratory motion signals detected from the data of FIG. 1A according to an exemplary embodiment of the present disclosure.
FIG. 1C is an exemplary diagram illustrating how data can be sorted according to an exemplary embodiment of the present disclosure.

Throughout the drawings, the same reference numerals and characters, unless otherwise stated, can be used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and appended claims.

DETAILED DESCRIPTION OF EXEMPLARY EMBODIMENTS

The exemplary system, method and computer-accessible medium can include a free-breathing cine MRI framework that can sort and synchronize cardiac and respiratory motion into two separate dimensions, followed by an exemplary joint multi-coil compressed sensing reconstruction (see, e.g., Reference 6) (e.g., image reconstruction) on the higher dimensional data set, using different sparsity constraints on respiratory and cardiac motion dimensions. Data can be continuously acquired using a golden-angle radial sampling procedure, and reconstructed separately, but with synchronized cardiac and respiratory motion dimensions, facilitating imaging of cardiac cycles with differing lengths. Specifically for the case of arrhythmias, both "normal" and "ectopic" cardiac cycles can be distinguished according to the length of cardiac cycles and grouped for separated reconstruction, which can provide additional information for potential clinical use.

Exemplary Method 1

An exemplary cardiac imaging protocol was performed on two volunteers (e.g., males, age=27/30) during consistent free breathing, without any external gating/triggering and preparation, on a 1.5 T MRI scanner (e.g., Avanto, Siemens). Data was continuously acquired for approximately 15 seconds in a middle ventricular short-axis ("SAX") plane, a long-axis ("LAX") plane and an aortic root ("ART") plane, using a two-dimensional ("2D") b-SSFP pulse sequence with golden-angle radial k-space sampling order. Imaging parameters included: (i) spatial resolution=2×2 mm, (ii) time of repetition (TR)/echo time (TE)=2.8/1.4 ms, (iii) flip angle ("FA")=70°, (iv) slice thickness=8 mm and (v) bandwidth=1375 Hz/pixel. The temporal evolution of the central k-space position (e.g., $k_x=k_y=0$) in each spoke (e.g., element 105 in, FIG. 1A) was used to estimate both cardiac contraction and respiration from coil-elements that were close to the heart and diaphragm, respectively. (See, e.g., FIG. 1B). (See, e.g., Reference 7). Raw data was then sorted into an expanded dataset containing two dynamic dimensions for cardiac and respiratory motion states, respectively.

FIG. 1B illustrates an exemplary graph of cardiac and respiratory signals. For example, as shown in FIG. 1B, each rectangular block (e.g., blocks 110, 115, 120 and 125) can represent an individual cardiac phase from a short "snapshot" period (e.g., about 15 consecutive spokes to produce "real-time" images) in different cardiac cycles. Data can be sorted into a higher dimensional matrix using the cardiac motion signal (see, e.g., FIG. 1C), followed by a second sorting procedure along the respiratory dimension from expiration to inspiration, and optionally back to expiration using the respiratory motion signal (e.g., this operation can be performed within each long box 130 shown in FIG. 1C). Reconstruction was performed by minimizing the objective function $\|E \cdot X - Y\|_2 + \lambda_1 \|T_1 \cdot X\|_1 + \lambda_2 \|T_2 \cdot x\|_1$, where X can be the sorted image to be jointly reconstructed with both cardiac and respiratory dimensions, Y can be the sampled k-space data in radial k-space and E can be the non-uniform Fast-Fourier Transform ("NUFFT") operator incorporating the coil sensitivities. (See, e.g., Reference 8). T1 and T2 can be sparsifying transforms (e.g., total variation) performed along cardiac and respiratory dimensions, respectively, and $\lambda 1$ and $\lambda 1$ can be the corresponding regularization parameters, which can be empirically selected. A 5th order temporal medial or median filter was used to remove the residual streaking artifact. For comparison purposes, standard real-time cine reconstructions were also performed. (See, e.g., Reference 9).

Exemplary Method 2

Figure 4:
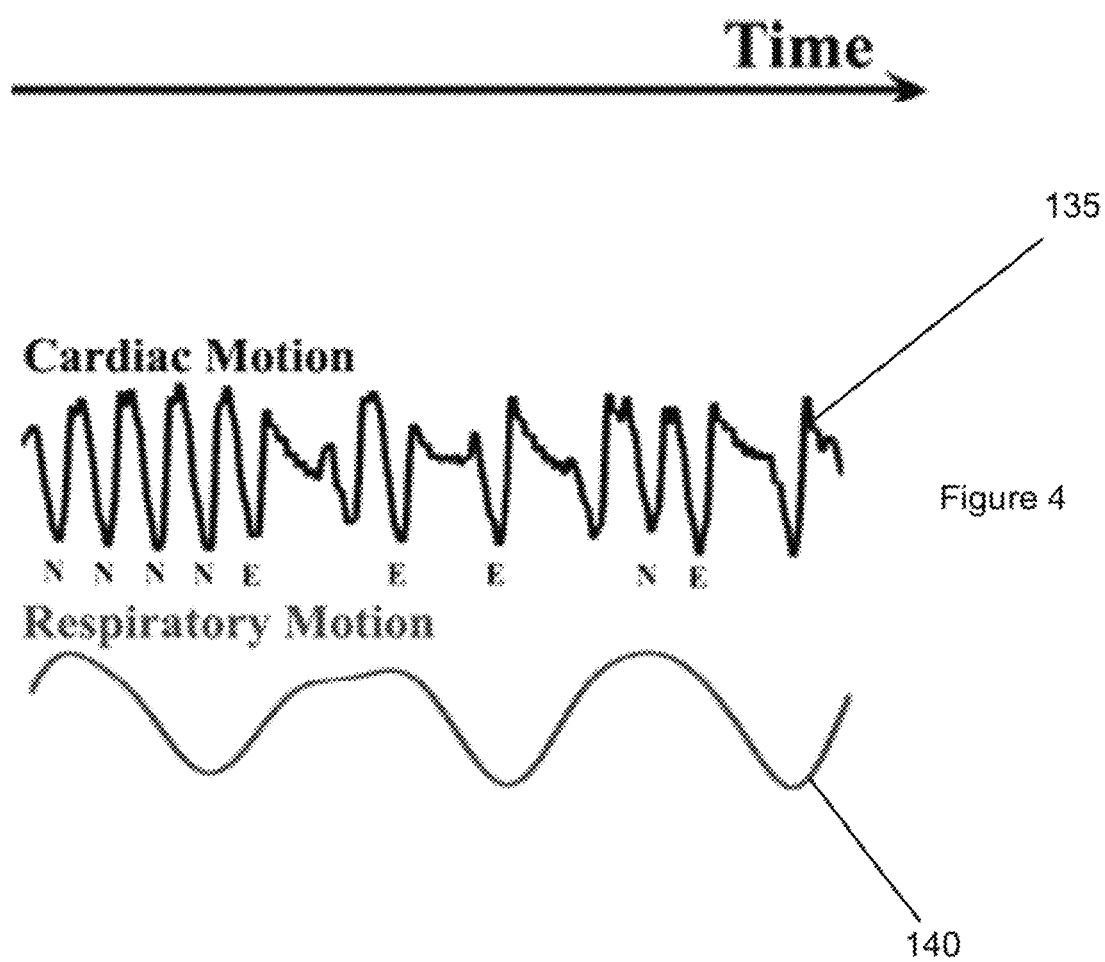
FIG. 4 is an exemplary diagram illustrating cardiac and respiratory motion detection in the presence of arrhythmias according to an exemplary embodiment of the present disclosure.

Both breath-hold cine MRI (e.g., Cartesian, retrospective ECG-gating) and free-breathing breathing cine MRI (e.g., golden-angle radial, no external gating/triggering) pulse sequences were implemented with b-SSFP readouts on a 1.5 T MRI scanner (e.g., Avanto, Siemens) equipped with a 12-element receive coil array. Exemplary relevant imaging parameters for breath-hold cine were, for example: (i) spatial resolution=1.8×1.8 mm, (ii) slice thickness=8 mm, (iii) TR/TE=2.5/1.25 ms, (iv) FA=50-70° and (v) BW=1305 Hz/pixel. Relevant imaging parameters for free breathing cine were: (i) spatial resolution=2×2 mm², (ii) slice thickness=8 mm, (iii) TR/TE≈2.8/1.4 ms, (iv) FA=70°, (v) BW=1375 Hz/pixel. Exemplary cardiac imaging was performed on 14 patients (e.g., mean age=56). 7 patients had normal sinus rhythm, 7 patients had arrhythmias (e.g., 4 bigeminy PVCs, 2 atrial fibrillation, 1 second degree block). SAX and one 4 chamber LAX cine image set were acquired on each patient; the acquisition time for both sequences was about 12 to about 15 seconds for one slice. Breath-hold cine image reconstruction was performed on-line in the scanner, and free-breathing cine image reconstruction was performed off-line in MATLAB (e.g., MathWorks, MA). Specifically, for free-breathing cine imaging, the k-space centers (e.g., $k_x=k_y=0$) in each spoke (e.g., element 105 in FIG. 1A) were used to extract physiological motion signals, including cardiac contraction signal 135 and respiration signal 140 simultaneously (see, e.g., FIG. 4), from coil elements which were close to the heart and diaphragm, respectively, (See, e.g., References 12 and 13). A local minimum in central-k-space signal was detected as end-systole positions. Using the detected motion signals, data were retrospectively sorted and synchronized to jointly reconstruct separate cardiac cycles with different lengths at different respiratory states. An exemplary multi-coil compressed sensing approach (see, e.g., References 14 and 15) was used to reconstruct the undersampled datasets, employing different total variation constraints along cardiac and respiratory dimensions, respectively. A $5^{th}$ order temporal medial filter was used to further remove the residual streaking artifacts. All the reconstructed datasets were blinded and randomized for image quality assessment by two radiologists, with scoring criteria as following: 5: excellent, 4: very good, 3: good, 2: poor, 1: non-diagnostic. Results from two readers were averaged (e.g., represented by mean±standard deviation) and divided into two groups. One group with normal sinus rhythm and the other group with arrhythmias.

Exemplary Results

Figure 2:
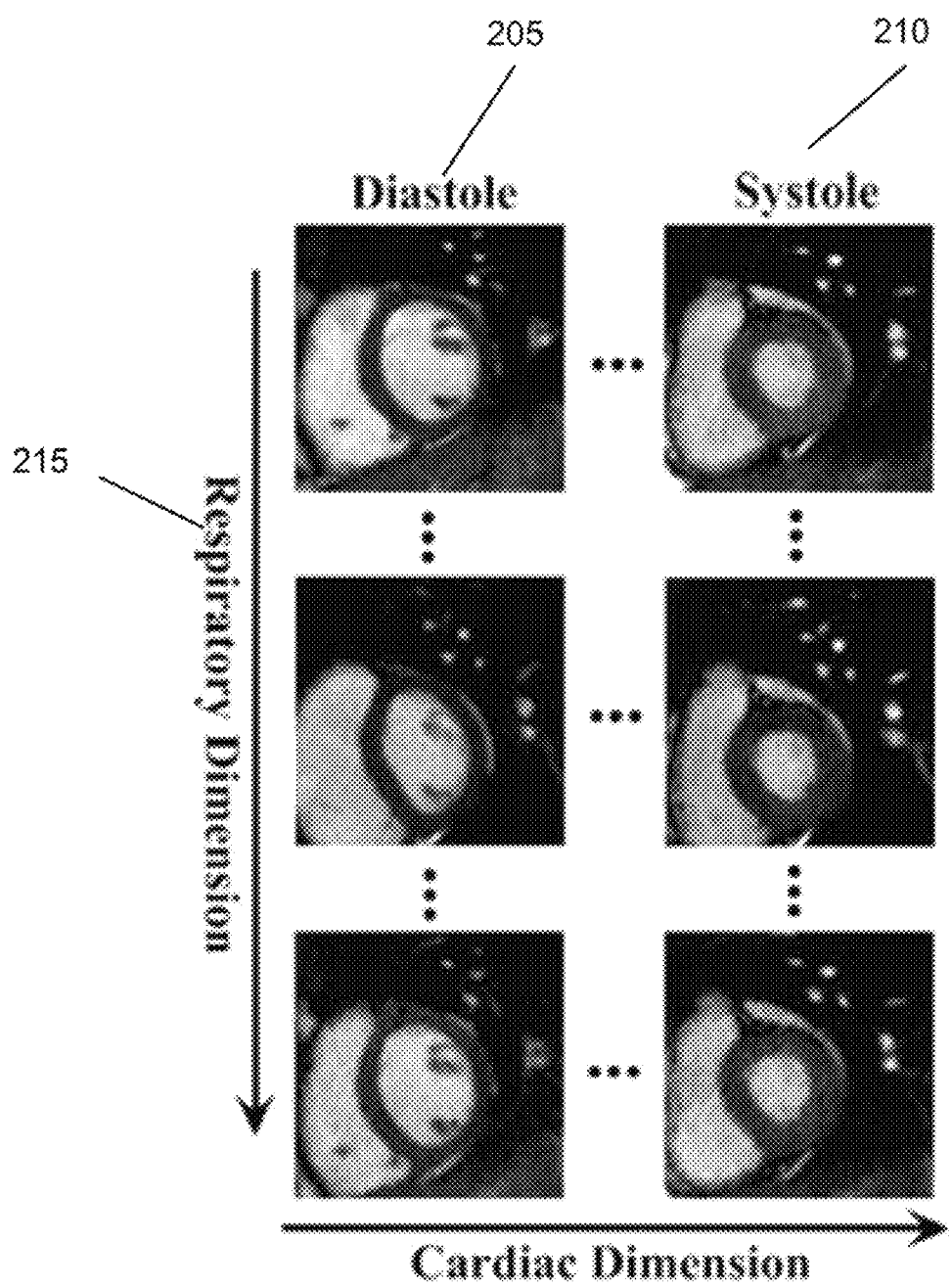
FIG. 2 is a set of exemplary images illustrating different cardiac phases and respiratory states in cardiac cine imaging according to an exemplary embodiment of the present disclosure.
Figure 3:
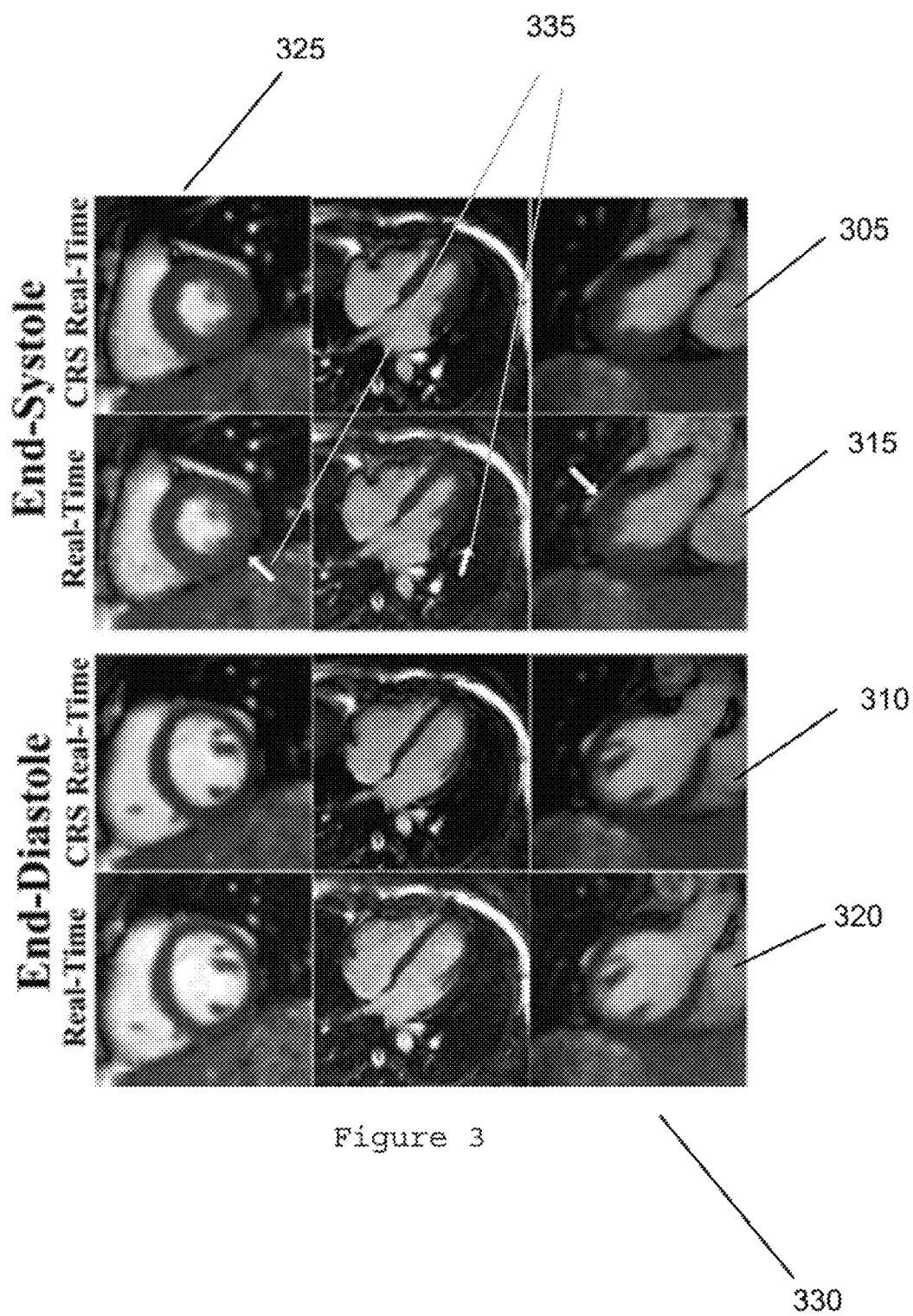
FIG. 3 is a set of images illustrating a comparison of cardiac cine images with cardio-respiratory synchronization according to an exemplary embodiment of the present disclosure.

FIG. 2 shows reconstructed SAX cardiac cine images, for diastole 205 and systole 210, at different cardiac phases and respiratory states, with cardio-respiratory synchronization. As shown, the myocardial wall can be moving along the respiratory dimension 215 even at the same cardiac phase, which can indicate that additional functional information can be obtained by performing the exemplary system, method and computer-accessible medium with cardio-respiratory sorting and synchronization. FIG. 3 illustrates a comparison of exemplary real-time cine images with synchronized cardiac and respiratory motion/sparsity 305 and 310 to the standard real-time cine images 315 and 320, reconstructed at end-systolic phase 325 and end-diastolic phase 330 in different imaging planes. Exemplary results with cardio-respiratory synchronization indicate improved image quality and less residual artifact over standard real-time cine imaging exploiting only one-dimensional temporal sparsity. Arrows 335 in FIG. 3 illustrate some residual artifacts in the standard real-time image reconstruction.

Figure 5:
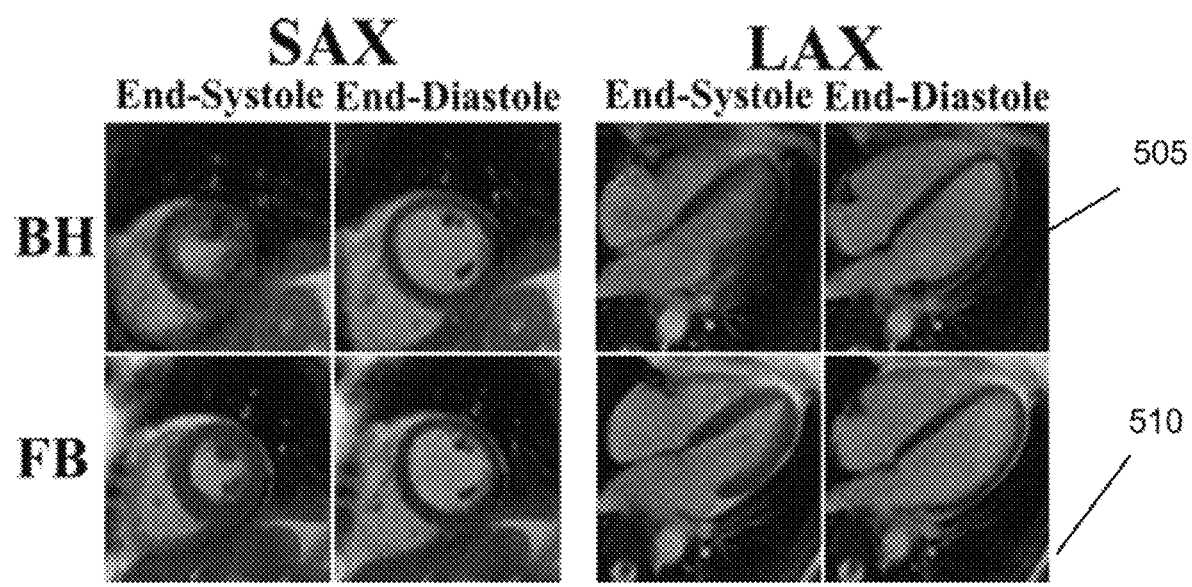
FIG. 5 is a set of exemplary images illustrating a comparison between breath-hold cine imaging with retrospective ECG-gating and free-breathing cine imaging with cardio-respiratory synchronization according to an exemplary embodiment of the present disclosure.
Figure 6:
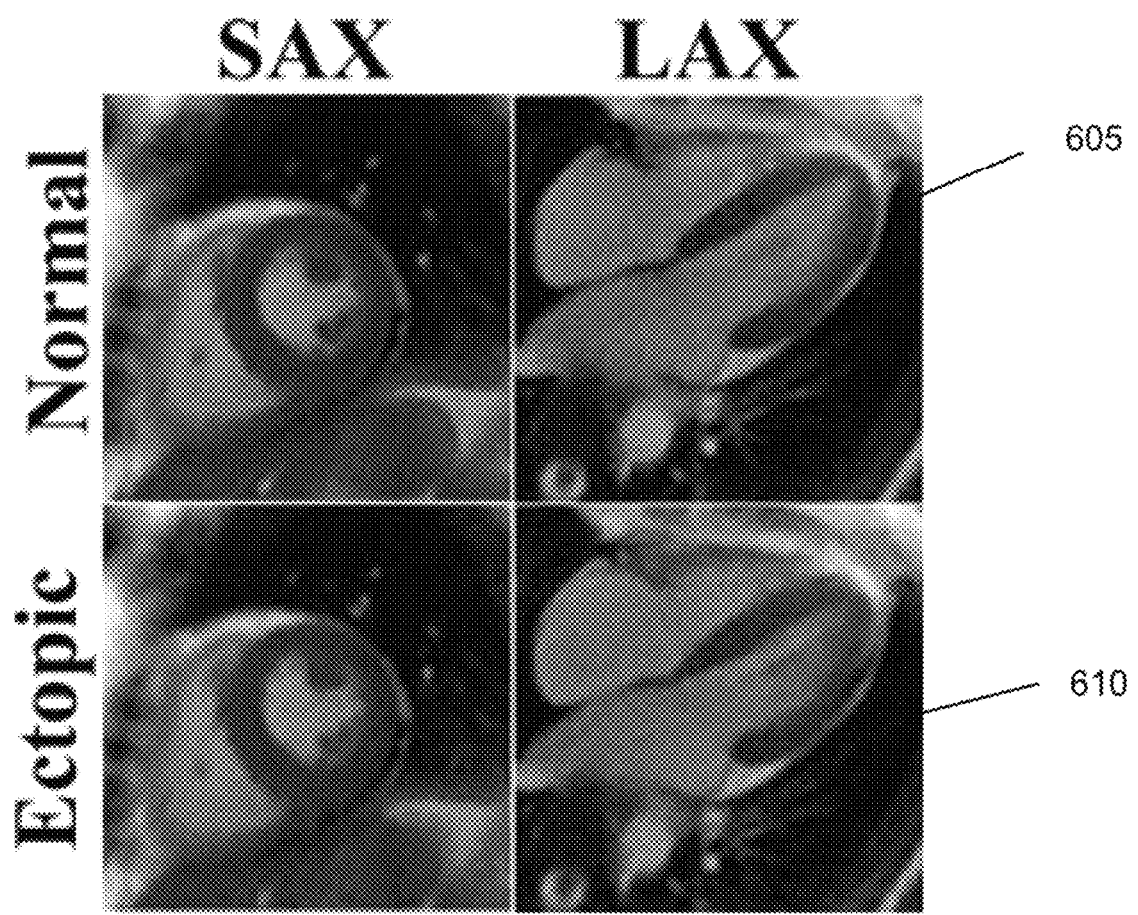
FIG. 6 is a set of exemplary images illustrating reconstruction of free-breathing end-systolic cardiac phases from both "normal" and "ectopic" cardiac cycles according to an exemplary embodiment of the present disclosure.

FIG. 5 shows both breath-hold cine images 505 and free-breathing cine images 510 of one patient with 2nd degree block, according to an exemplary embodiment of the present disclosure. When compared to the clinical standard approach, which can be sensitive to arrhythmias, the exemplary free-breathing system, method and computer-accessible medium produced superior image quality, due to the ability to differentiate "normal" and "ectopic" cycles, as also seen from Table 1 below. (See, e.g., group 2). For patients with normal sinus rhythm, the exemplary results from both approaches can be effective with adequate diagnostic image quality. (See, e.g., see Table 1, Group 1). FIG. 6 shows exemplary free-breathing cine images reconstructed from both "normal" cycles 605 and "ectopic" cycles 610 on the same patient as illustrated in FIG. 5.

TABLE 1

Image quality comparison between breath-hold and free-breathing cine Images. Group 1 includes patients with normal sinus rhythm and group 2 includes patients with arrhythmias.

| Technique | Group 1 | Group 2 |
|---|---|---|
| BH | 3.82 ± 0.52 | 1.96 ± 0.83 |
| FB | 3.06 ± 0.58 | 3.05 ± 0.69 |

BH: breath-hold.
FB: free-breathing

Exemplary Discussion

Separating cardiac and respiratory motion can improve the sparsity of representation, and thus the acceleration capability and performance for compressed sensing. Instead of incorporating a registration procedure for respiratory motion correction, the exemplary system, method and computer-accessible medium, according to an exemplary embodiment of the present disclosure, can use joint reconstruction of respiratory motion components to improve the reconstruction in a compressed sensing framework. The exemplary system, method and computer-accessible medium, according to an exemplary embodiment of the present disclosure, can produce high quality cardiac cine imaging during free-breathing, and can provide additional functional information, which can enable the investigation of the interactions between cardiac and respiratory cycles and their effects on cardiac function. For example, it can be used for evaluating patients with pericardial diseases that can have larger shifts of the interventricular septum with respiration, especially in deep breathing.

Figure 7:
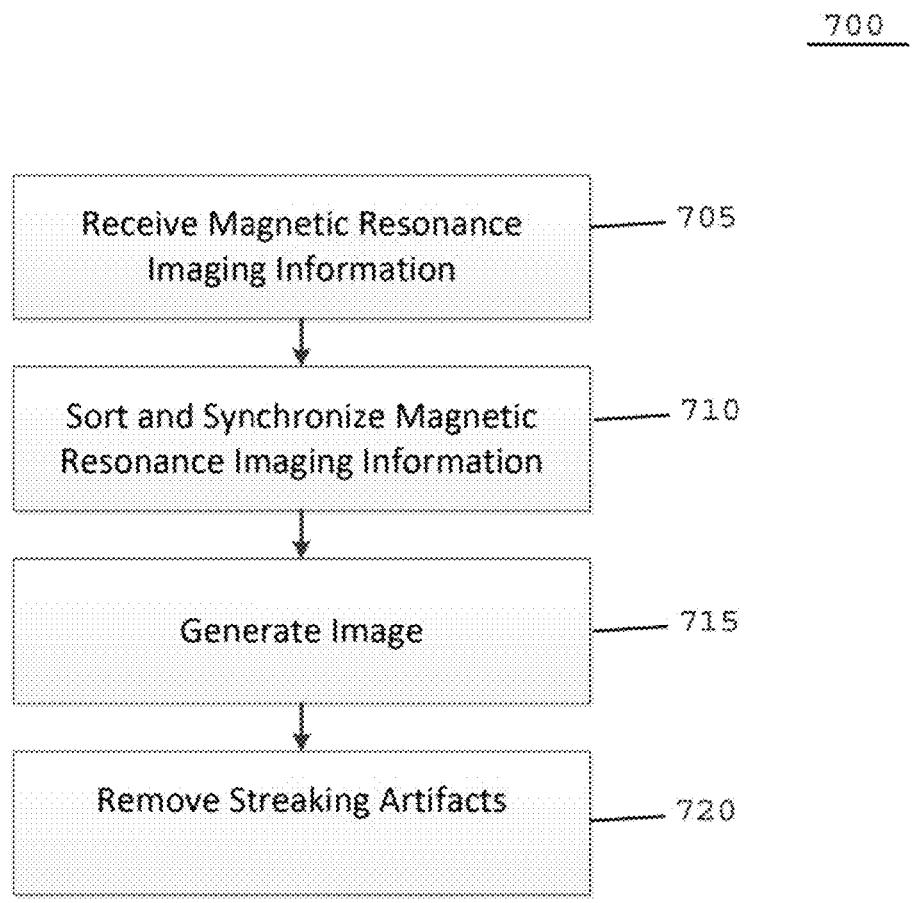
FIG. 7 is a flow diagram of an exemplary method for generating an image according to an exemplary embodiment of the present disclosure.
Figure 8:
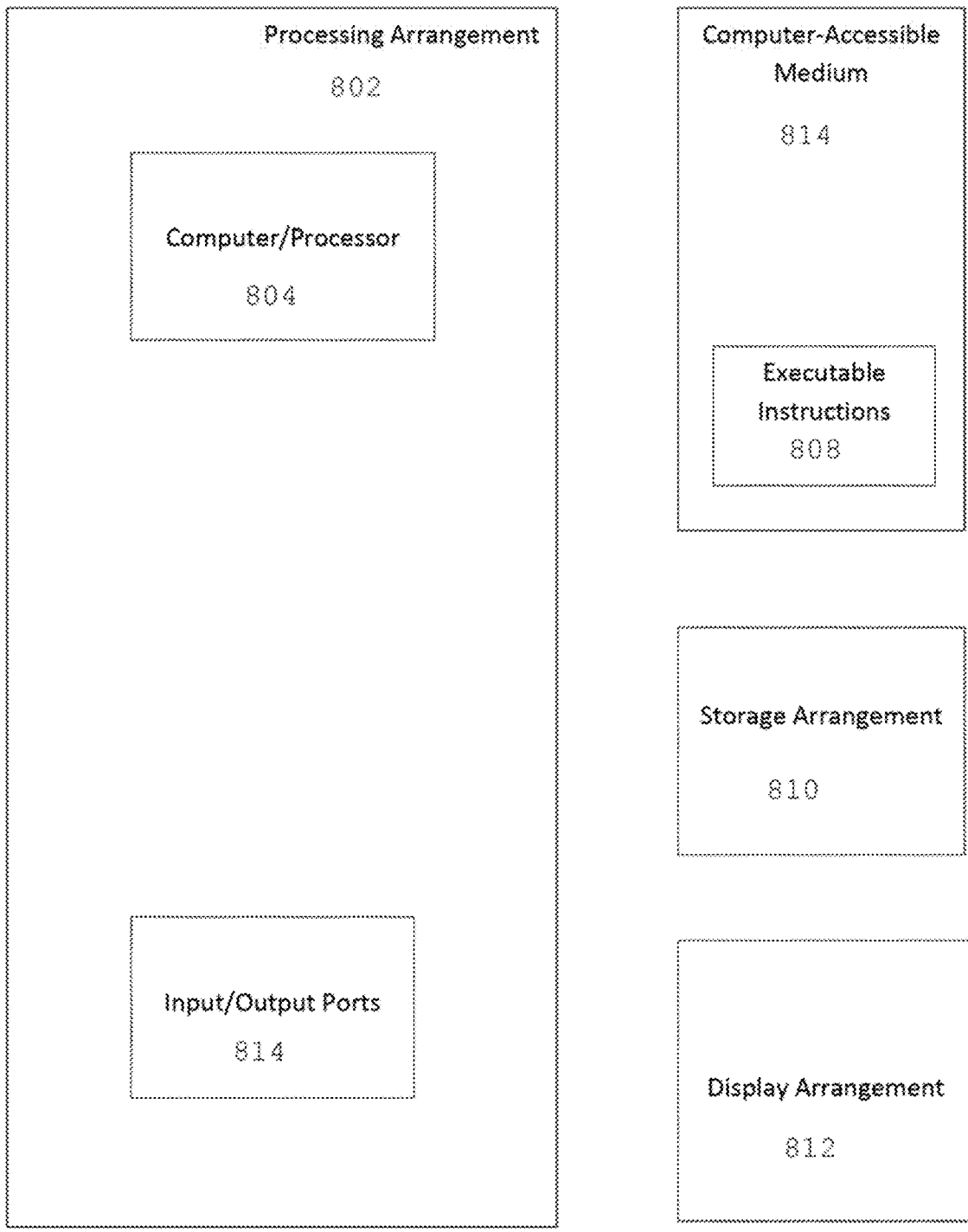
FIG. 8 is an illustration of an exemplary block diagram of an exemplary system in accordance with certain exemplary embodiments of the present disclosure.

FIG. 7 is a flow diagram of an exemplary method 700 for generating an image according to an exemplary embodiment of the present disclosure, which can be performed by an exemplary system shown in FIG. 8. For example, at procedure 705, MRI information regarding tissue, which can be based on a golden-angle radial sampling procedure, can be received. The MRI information can be sorted and synchronized at procedure 710, for example, based on a length of a cardiac cycle of a patient and/or a respiratory dimension of the patient. At procedure 715, an image of the tissue can be generated, and residual streaking artifacts can be removed at procedure 720, which can be performed at the same time as the image generation in procedure 715.

Exemplary Conclusion

The exemplary system, method and computer-accessible medium, according to an exemplary embodiment of the present disclosure, can be used for reconstructing cardiac cine images in patients with arrhythmias, with superior image quality than the standard breath-hold approach, using free-breathing compressed sensing MRI with physiological motion synchronization. In addition, the exemplary system, method and computer-accessible medium can be used to reconstruct both "normal" and "ectopic" cardiac cycles in those patients. The "ectopic" cycles can produce different clinically useful information, for example, due to the naturally varying length of cardiac cycles, which can produce changes in the cardiac function, or different contraction patterns of ectopic beats.

FIG. 8 shows a block diagram of an exemplary embodiment of a system according to the present disclosure. For example, exemplary procedures in accordance with the present disclosure described herein can be performed by a processing arrangement and/or a computing arrangement 802. Such processing/computing arrangement 802 can be, for example, entirely or a part of, or include, but are not limited to, a computer/processor 804 that can include, for example, one or more microprocessors, and use instructions stored on a computer-accessible medium (e.g., RAM, ROM, hard drive, or other storage device).

As shown in FIG. 8, for example, a computer-accessible medium 806 (e.g., as described herein above, a storage device such as a hard disk, floppy disk, memory stick, CD-ROM, RAM, ROM, etc., or a collection thereof) can be provided (e.g., in communication with the processing arrangement 802). The computer-accessible medium 806 can contain executable instructions 808 thereon. In addition or alternatively, a storage arrangement 810 can be provided separately from the computer-accessible medium 806, which can provide the instructions to the processing arrangement 802 so as to configure the processing arrangement to execute certain exemplary procedures, processes and methods, as described herein above, for example.

Further, the exemplary processing arrangement 802 can be provided with or include an input/output arrangement 814, which can include, for example, a wired network, a wireless network, the internet, an intranet, a data collection probe, a sensor, etc. As shown in FIG. 8, the exemplary processing arrangement 802 can be in communication with an exemplary display arrangement 812, which, according to certain exemplary embodiments of the present disclosure, can be a touch-screen configured for inputting information to the processing arrangement in addition to outputting information from the processing arrangement, for example. Further, the exemplary display 812 and/or a storage arrangement 810 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

[1] Carr J C et al. Radiology 2001: 219:828-834.
[2] Hansen M S et al. MRM 2012 September; 68(3):741-50.
[3] Usman M et al. MRM 2013 August; 70(2):504-16.
[4] Beer M, et al. Int J Cardiol 2010; 145380-382.
[5] Feng L, et al. MRM 2013 July; 70(1):64-74.
[6] Otazo R et al. MRM 2010 September; 64(3):767-76.
[7] Liu J et al. MRM 2010 63(5):1230-1237.
[8] Fessler. IEEE T-SP 2003 51(2):560-74.
[9] Feng L, et al. ISMRM 2012, p 225.
[10] Feng L, et al. MRM 2013 July; 70(1):64-74.
[11] Feng L, et al. ISMRM 2012 p 255.
[12] Liu J, et al. MRM 2010; 63: 1230-1237.
[13] Feng L, et al. ISMRM 2013 p 606.
[14] Otazo R et al. MRM 2010 September; 64(3): 767-76.
[15] Feng L et al. MRM 2013 doi: 10.1002/mrm/24980.

What is claimed is:

1. A non-transitory computer-accessible medium having stored thereon computer-executable instructions for generating at least one image of at least one tissue, wherein, when a computer arrangement executes the instructions, the computer arrangement is configured to perform procedures comprising:
   receiving magnetic resonance imaging (MRI) information regarding the at least one tissue based on a golden-angle radial sampling procedure;
   electronically sorting and synchronizing the MRI information into at least two dimensions which include a respiratory dimension and a cardiac dimension; and
   generating the at least one image of the at least one tissue based on the sorted and synchronized information.

2. The computer-accessible medium of claim 1, wherein the at least one tissue includes cardiac tissue and respiratory-affected tissue.

3. The computer-accessible medium of claim 2, wherein the MRI information includes a motion of the cardiac tissue and a motion of the respiratory tissue.

4. The computer-accessible medium of claim 1, wherein the at least two dimensions are two separated dimensions.

5. The computer-accessible medium of claim 1, wherein computer arrangement is further configured to generate the at least one image based on a compressed sensing procedure.

6. The computer-accessible medium of claim 5, wherein the compressed sensing procedure is a joint multi-coil compressed sensing procedure.

7. The computer-accessible medium of claim 5, wherein the computer arrangement is further configured to perform the compressed sensing procedure only on one of the at least two dimensions.

8. The computer-accessible medium of claim 7, wherein the one of the at least two dimensions is a higher of the at least two dimensions.

9. The computer-accessible medium of claim 8, wherein the computer arrangement is further configured to perform the compressed sensing procedure using sparsity constraints on the higher of the at least two dimensions.

10. The computer-accessible medium of claim 8, wherein the at least one tissue includes cardiac tissue and respiratory tissue, and wherein the sparsity constraints for the cardiac tissue are different than the sparsity constraints for the respiratory tissue.

11. The computer-accessible medium of claim 7, wherein the computer arrangement is further configured to perform the compressed sensing procedure on both of the at least two dimensions.

12. The computer-accessible medium of claim 1, wherein the at least two dimensions include at least two motion related dimensions.

13. The computer-accessible medium of claim 1, wherein the sorting procedure includes sorting the MRI information based on a length of at least one cardiac cycle of a patient to whom the at least one tissue belongs.

14. The computer-accessible medium of claim 1, wherein the sorting procedure includes sorting the MRI information based on the respiratory dimension of a patient to whom the at least one tissue belongs.

15. The computer-accessible medium of claim 1, wherein the respiratory dimension is from an expiration to an inspiration of the patient.

16. The computer-accessible medium of claim 1, wherein the golden-angle radial sampling procedure is a golden-angle radial k-space sampling procedure.

17. The computer-accessible medium of claim 1, wherein the computer arrangement is further configured to remove at least one residual streaking artifact from the at least one image.

18. The computer-accessible medium of claim 1, wherein the computer arrangement is further configured to remove the at least one residual streaking artifact using at least one of (i) a 5th order temporal filter, or (ii) a 5th order median filter.

19. A method for generating at least one image of at least one tissue, comprising:
receiving magnetic resonance imaging (MRI) information regarding the at least one tissue based on a golden-angle radial sampling procedure;
electronically sorting and synchronizing the MRI information into at least two dimensions which include a respiratory dimension and a cardiac dimension; and
using a computer hardware arrangement, generating the at least one image of the at least one tissue based on the sorted and synchronized information.

20. A system for generating at least one image of at least one tissue, comprising:
a computer hardware arrangement configured to:
receive magnetic resonance imaging (MRI) information regarding the at least one tissue based on a golden-angle radial sampling procedure;
electronically sort and synchronizing the MRI information into at least two dimensions which include a respiratory dimension and a cardiac dimension; and
generate the at least one image of the at least one tissue based on the sorted and synchronized information.

21. A non-transitory computer-accessible medium having stored thereon computer-executable instructions for generating at least one image of at least one tissue, wherein, when a computer arrangement executes the instructions, the computer arrangement is configured to perform procedures comprising:
receiving imaging information regarding the at least one tissue based on a radial sampling procedure;
electronically sorting and synchronizing the imaging information into at least two dimensions which include a respiratory dimension and a cardiac dimension; and
generating the at least one image of the at least one tissue based on the sorted and synchronized information.

22. The computer-accessible medium of claim 21, wherein the imaging information includes at least one of (i) magnetic resonance imaging information, (ii) positron emission tomography information, (iii) computed tomography information or (iv) single-photon emission computed tomography information.

23. The computer-accessible medium of claim 21, wherein the radial sampling procedure includes a golden-angle radial sampling procedure.

* * * * *